(12) United States Patent
Goto et al.

(10) Patent No.: US 6,277,366 B1
(45) Date of Patent: Aug. 21, 2001

(54) RELEASE-SUSTAINING AGENT FOR DRUGS AND SUSTAINED-RELEASE PHARMACEUTICAL COMPOSITION

(75) Inventors: Takeshi Goto; Hiroshi Sorimachi; Kazuhisa Yoshitake; Toshio Itoyama, all of Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/530,910

(22) PCT Filed: Oct. 30, 1998

(86) PCT No.: PCT/JP98/04926

§ 371 Date: Jun. 23, 2000

§ 102(e) Date: Jun. 23, 2000

(87) PCT Pub. No.: WO99/24072

PCT Pub. Date: May 20, 1999

(30) Foreign Application Priority Data

Nov. 10, 1997 (JP) .................................................. 9-307371

(51) Int. Cl.[7] ........................ A61K 31/74; A61K 31/785; A61K 9/22
(52) U.S. Cl. .................... 424/78.1; 424/78.12; 424/468; 424/78.35
(58) Field of Search ............................. 424/78.12, 78.35, 424/489, 440, 497, 468, 490, 483

(56) References Cited

U.S. PATENT DOCUMENTS

| | | |
|---|---|---|
| 3,138,525 | 6/1964 | Koff . |
| 4,460,577 | 7/1984 | Moro et al. . |
| 4,814,354 * | 3/1989 | Ghebre-Sellassie et al. ........ 424/440 |
| 5,032,393 | 7/1991 | Douglas et al. . |
| 5,665,348 * | 9/1997 | Okayama et al. ................ 424/78.35 |
| 5,840,339 * | 11/1998 | Kunin ................................... 424/489 |
| 6,022,533 * | 2/2000 | Goto et al. ......................... 424/78.12 |

FOREIGN PATENT DOCUMENTS

| | | |
|---|---|---|
| 857193 | 12/1960 | (GB) . |
| 1218102 | 1/1971 | (GB) . |
| 55-100313 | 7/1980 | (JP) . |
| 2-111719 | 4/1990 | (JP) . |
| 3-52824 | 3/1991 | (JP) . |
| 8-208750 | 8/1996 | (JP) . |

* cited by examiner

Primary Examiner—Thurman K. Page
Assistant Examiner—Blessing Fubara
(74) Attorney, Agent, or Firm—Pillsbury Winthrop LLP

(57) ABSTRACT

A sustainedly releasing agent for medicines comprising a non-crosslinked type anion-exchange resin represented by the general formula (I):

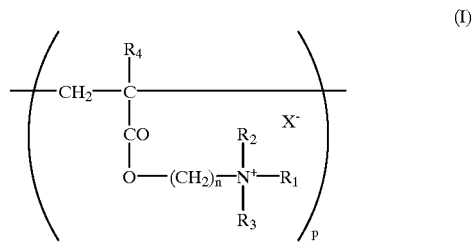

wherein $R_1$ represents aralkyl or alkyl, each of $R_2$ and $R_3$ represents lower alkyl, $R_4$ represents a hydrogen atom or lower alkyl, $X^-$ represents a physiologically acceptable counter ion, n represents 1–3, and p represents a mean degree of polymerization, respectively, as well as a sustainedly released medicinal composition comprising the sustainedly releasing agent and a hypolipidemic agent.

5 Claims, 2 Drawing Sheets

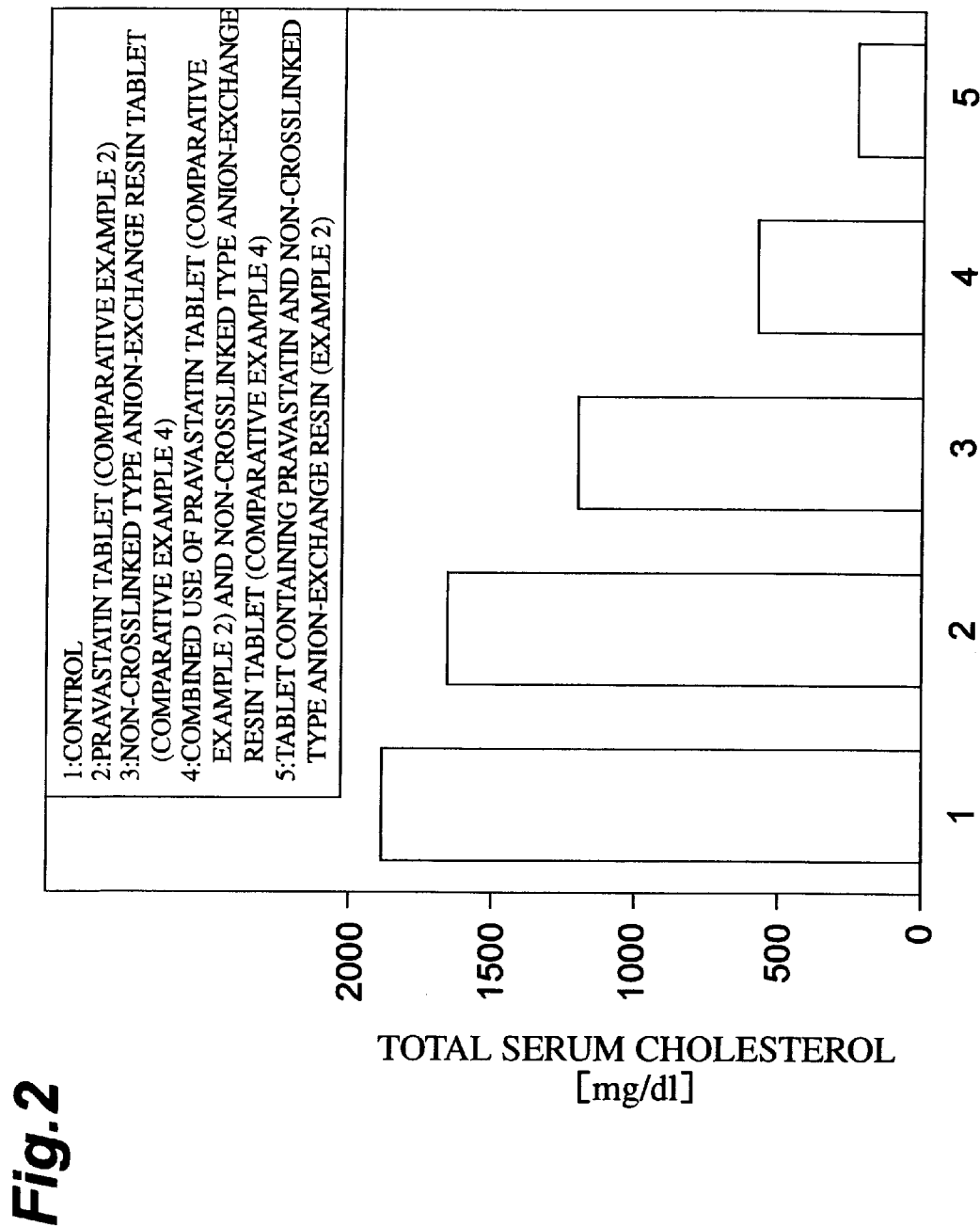

RELEASE-SUSTAINING AGENT FOR DRUGS AND SUSTAINED-RELEASE PHARMACEUTICAL COMPOSITION

TECHNICAL FIELD

This invention relates to a sustainedly releasing agent for medicines and a sustainedly released medicinal composition containing it. More particularly, the invention relates to a sustainedly releasing agent for medicines comprising a specific non-crosslinked type anion-exchange resin, as well as to a sustainedly released medicinal composition useful for the prevention or treatment of hyperlipidemia which contains the sustainedly releasing agent for medicines and a medicine having a hypolipidemic effect.

BACKGROUND ART

Hitherto, several patents have disclosed methods for binding active ingredients to ion-exchange resins. For example, active ingredients are immobilized to cationic or anionic polystyrene-divinyl benzene resins, as described in British Patent No. 857,193. Several other patents also describe methods for coating active ingredient/resin complexes. For example, U.S. Pat. No. 3,138,525 discloses a method for concealing the taste of amprotopine by forming a complex with a cationic resin and coating it with wax. Also, British Patent No. 1,218,102 describes a method for coating with a device such as an air-fluidized bed, a complex in which a cationic active ingredient is immobilized to an anionic resin. Further, Japanese Patent Application Laid-Open Gazette No. Hei 3-52824 describes a sustainedly releasing medicine capable of regulating the release rate of an active ingredient, which medicine comprises an active ingredient/ion-exchange resin complex coated with an ionic polymer having the polarity opposite to that of the resin.

DISCLOSURE OF THE INVENTION

However, where the active ingredients are anionic or liposoluble medicines, sustainedly releasing agents that exert a sufficient sustained release action have not yet been developed. Particularly, it has been hoped that sustainedly releasing agents useful for the sustained release of medicines for the prevention or treatment of hyperlipidemia be developed where in the past the combined use of plural hypolipidemic medicines was difficult while sufficiently avoiding their side effects.

This invention has been made in consideration of the problems inherent in the above-stated prior art; and it aims at providing a sustainedly releasing agent capable of exerting a sufficient sustained release action when the active ingredient is an anionic or liposoluble medicine, which is particularly useful for the sustained release of a medicine for the prevention or treatment of hyperlipidemia, as well as a sustainedly released medicinal composition containing the agent.

As a result of extensive investigations that were repeated with the aim of accomplishing the above-mentioned object, the present inventors have discovered the findings as described below and thus have come to completing the invention. Specifically, it has been discovered that non-crosslinked type anion-exchange resins represented by the following general formula (II):

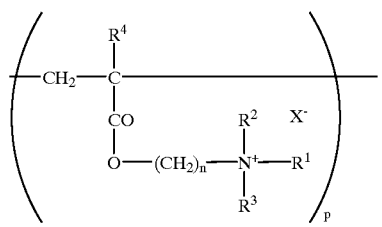

wherein
$R_1$ represents benzyl group or an alkyl group of 1–20 carbons; $R_2$ and $R_3$ may be the same or different, and each represents a lower alkyl group of 1–4 carbons; $R_4$ represents a hydrogen atom or a lower alkyl group; $X^-$ represents a physiologically acceptable counter ion; n represents 1–3; and p represents a mean degree of polymerization of 10–10,000, respectively, as described in Japanese Patent Application Laid-Open Gazette No. Hei 8-208750 and which were developed by the present inventors as blood cholesterol lowering agents that solves the drawbacks of bile acid adsorbents are unexpectedly useful as sustainedly releasing agents for medicines particularly where anionic or liposoluble medicines are chosen as active ingredients, because they have hydrophobic groups while being non-crosslinked type anion-exchange resins; and the discovery has led to the invention.

The sustainedly releasing agent (sustained-releasing agent) for medicines of this invention is that comprising a non-crosslinked type anion-exchange resin (a nonbridged type anion-exchange resin) represented by the following general formula (I):

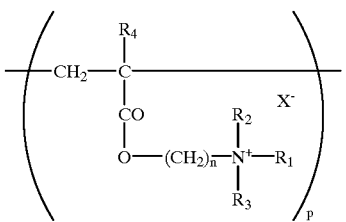

wherein
$R_1$ represents a moiety selected from the group consisting of aralkyl groups of 7–10 carbons and alkyl groups of 1–20 carbons; $R_2$ and $R_3$ may be the same or different, and each represents a lower alkyl group of 1–4 carbons; $R_4$ represents a hydrogen atom or a lower alkyl group; $X^-$ represents a physiologically acceptable counter ion; n represents 1–3; and p represents a mean degree of polymerization, respectively.

Further, the sustainedly released medicinal composition (sustained-releasing medicinal composition) of this invention is that comprising the sustainedly releasing agent that is comprised of the non-crosslinked type anion-exchange resin represented by the general formula (I) as described above and a medicine having a hypolipidemic effect.

Furthermore, this invention resides in the use of the non-crosslinked type anion-exchange resin represented by the above-mentioned general formula (I) as a sustainedly releasing agent for medicines.

BRIEF DESCRIPTION OF THE DRAWINGS

FIG. 2 is a graph showing the results of Test 2 on the control of the rise of blood cholesterol.

BEST MODE FOR CARRYING OUT THE INVENTION

Figure 1:
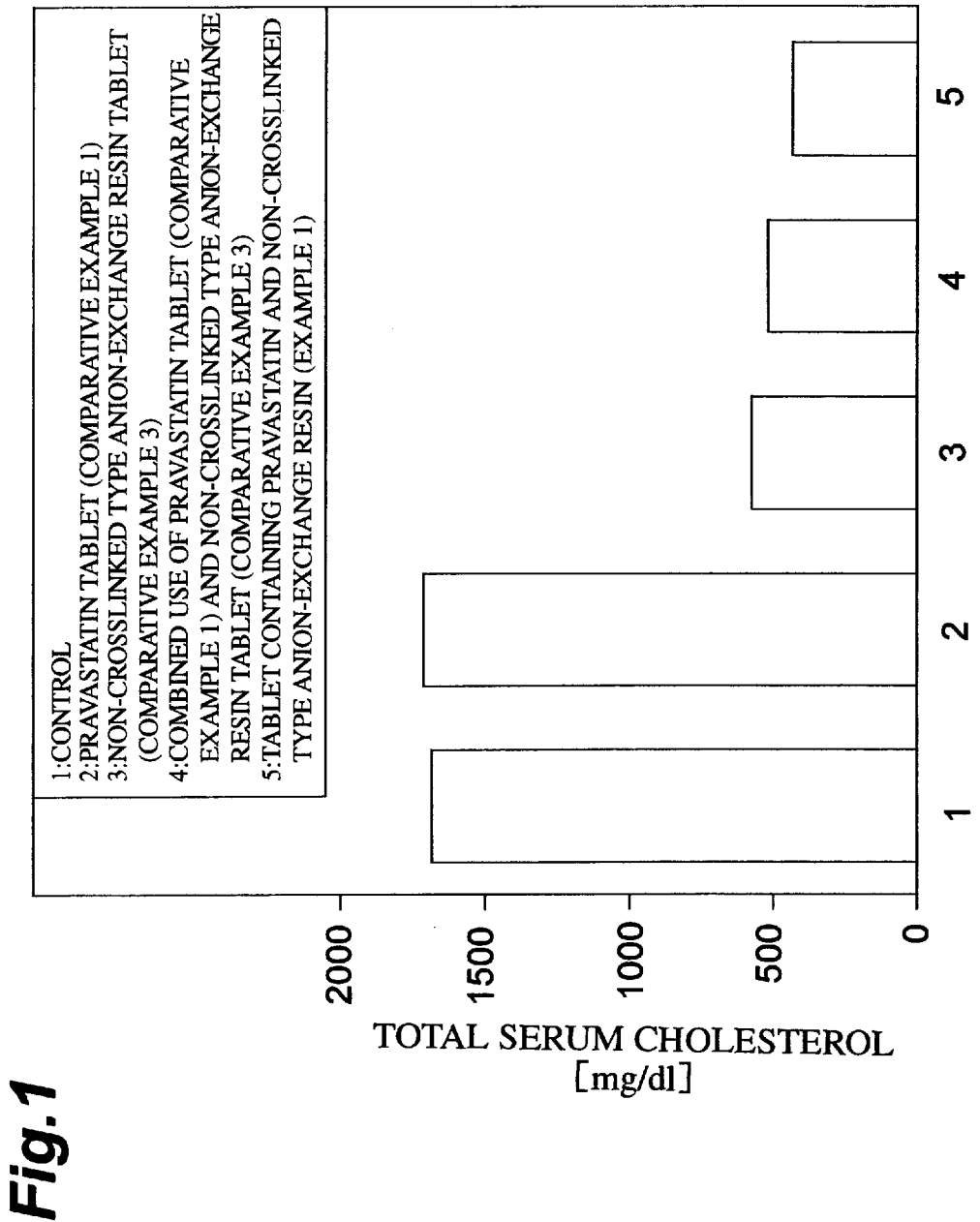
FIG. 1 is a graph showing the results of Test 1 on the control of the rise of blood cholesterol.

The sustainedly releasing agents for medicines of this invention comprise a non-crosslinked type anion-exchange resin represented by the general formula (I) as described above. In the above-mentioned general formula (I), substituent $R_1$ is an aralkyl groups of 7–10 carbons or an alkyl group of 1–20 carbons, and the aryl group of the aralkyl group may contain a substituent but is preferably nonsubstituted. In addition, the alkyl group may be a straight or branched chain type one. Among such aralkyl groups mentioned are benzyl, phenylethyl, and the like, with the benzyl being more preferable. Among such alkyl groups mentioned are methyl, ethyl, n-propyl, isopropyl, hexyl, dodecyl, octadecyl, eicosyl, and the like.

Substituents $R_2$ and $R_3$ may be the same or different and are each a lower alkyl group of 1–4 carbons, which may be a straight or branched chain type one. Among such lower alkyl groups mentioned are methyl, ethyl, n-propyl, isopropyl, n-butyl, isobutyl, and the like, with themethyl being more preferable.

Substituent $R_4$ is a hydrogen atom or a lower alkyl group and the lower alkyl group may be a straight or branched chain type one. Among such lower alkyl groups mentioned are methyl, ethyl, n-propyl, isopropyl, n-butyl, isobutyl, and the like. Such substituent $R_4$ is more preferably a hydrogen atom.

Although counter ion $X^-$ is not particularly limited insofar as it is a physiologically acceptable counter ion, mentioned are, for example, halide ion; anions of inorganic acid salts such as a sulfate, bicarbonate, and carbonate; and anions of organic acid salts such as a formate, acetate, propionate, malonate, succinate, fumarate, ascorbate, sulphonate, phosphate, glucuronate, and amino acid salts (e.g., aspartate and glutamate). Among them sulfate ion, phosphate ion, and halide ions (e.g., chloro, bromo and fluoro ions) are preferable with the chloro ion being particularly preferable.

Furthermore, "n" that is the structural unit of the methylene group (—$CH_2$—) is an integer of 1–3, preferably 2. Also, "p" in the general formula (I) as described above represents a mean degree of polymerization. When such mean degree of polymerization "p" is from 10 to 50,000, the sustained release action against a medicine tends to be greater, which is preferable. More preferably, "p" is from 20 to 30,000, most preferably from 20 to 20,000.

Among concrete examples of such non-crosslinked type anion-exchange resins, according to this invention, that are represented by the above-mentioned general formula (I), mentioned are for example as follows:

Poly(acryloyloxyethyl-N,N,N-trimethylammonium chloride);
Poly(methacryloyloxyethyl-N,N,N-trimethylammonium chloride);
Poly(acryloyloxyethyl-N,N-dimethyl-N-benzylammonium chloride);
Poly(methacryloyloxyethyl-N,N-dimethyl-N-benzylammonium chloride);
Poly(acryloyloxyethyl-N,N-dimethyl-N-hexylammonium chloride);
Poly(methacryloyloxyethyl-N,N-dimethyl-N-hexylammonium chloride);
Poly(acryloyloxyethyl-N,N-dimethyl-N-dodecylammonium chloride);
Poly(methacryloyloxyethyl-N,N-dimethyl-N-dodecylammonium chloride);
Poly(acryloyloxyethyl-N,N-dimethyl-N-octylammonium chloride); and
Poly(methacryloyloxyethyl-N,N-dimethyl-N-octylammonium chloride). Poly(acryloyloxyethyl-N,N-dimethyl-N-benzyl-ammonium chloride) is more preferable.

There are also no limitations to the method for producing a non-crosslinked type anion-exchange resin according to this invention. For example, it is possible to prepare a quaternary ammonium salt of the corresponding monomer and to produce the resin by polymerizing this in the presence of a polymerization initiator such as a radical polymerization agent.

The sustainedly releasing agent of this invention comprises a non-crosslinked type anion-exchange resin represented by the general formula (I) as described above; and although it can be used alone or in combination with other medicines, preferably it is used in a sustainedly released medicinal composition comprising the sustainedly releasing agent of this invention and a medicine. Also, it suffices that the sustainedly releasing agent as described above and the medicine are contained in a sustainedly released medicinal composition of this invention; and although their forms are not particularly limited, it is preferred that the medicine be dispersed, preferably almost in a homogeneous manner, in the sustainedly releasing agent as described above.

Although such medicines are not particularly limited, medicines having a hypolipidemic effect (hereinafter sometimes referred to as "hypolipidemic agent") may preferably be used in combination with the non-crosslinked type anion-exchange resins according to this invention as described above, because they have a cholesterol lowering effect of their own. Particularly, where the sustainedly releasing agent comprising a non-crosslinked type anion-exchange resin represented by the general formula (I) as described above is used in combination with a medicine for the prevention or treatment of hyperlipidemia, synergism of the blood cholesterol lowering effects is obtained, which is more preferable.

For hypolipidemic agents that are used in combination with the sustainedly releasing agents comprising non-crosslinked type anion-exchange resins of the general formula (I) as described above, preferred are those which completely differ from the bile acid adsorbents such as non-crosslinked type anion-exchange resins with respect to the mechanism of action. Among such hypolipidemic agents mentioned are probucol, clofibrate type medicines, nicotinic acid preparations, squalene synthetase inhibitors, squalene epoxidase inhibitors, hydroxymethylglutaryl coenzyme A (HMG-CoA) reductase inhibitors, acyl coenzyme A:cholesterol acyl transferase (ACAT) inhibitors, etc.; and the HMG-CoA reductase inhibitors are more preferable.

Particularly, the HMG-CoA reductase inhibitors have been in frequent use in recent years; and among others, they Cal lower the total serum cholesterol by about 15–20%, which makes it relatively easy to control serum cholesterol. Among such HMG-CoA reductase inhibitors mentioned are pravastatin (U.S. Pat. Nos. 4,346,227 and 4,410,629), cerivastatin (U.S. Pat. Nos. 5,006,530 and 5,177,080), lovastatin (U.S. Pat. Nos. 4,231,938 and 4,294,926), fluvastatin (U.S. Pat. Nos. 473,973 and 5,354,772), atrovastatin (U.S. Pat. No. 5,273,995), and simvastatin (U.S. Pat. No. 4,450,171). Anionic medicines like pravastatin are more preferable since they show a more sustained action.

In addition, there are serious cases where the total serum cholesterol exceeds 300 ml/dl, and the lowering of cholesterol by any single agents cannot be satisfactory. This is evident, for example, as described in the paper by D. R. Illingworth, "Clin. Chem. 34, No. 8, Supplement, B123–B132, 1988; entitled "Medicine Therapy for Hypercholesterolemia": "1 Two or three kinds of medicines whose mechanisms of action are different from each other can be combined for use in serious hypercholesterolemia. It is concluded that in patients suffering from serious hypercholesterolemia, currently available medicines can adequately lower their plasma cholesterol and thus can alter the progression of atherosclerosis at early stages." The sustainedly released medicinal compositions of this invention rely on the use of the above-mentioned hypolipidemic agents in combination with the sustainedly releasing agents comprising non-crosslinked type anion-exchange resins as described above which possess a cholesterol lowering effect of their own in addition to a sustained release action; and therefore, they are also useful from the standpoint of the combined use of medicines for the prevention or treatment of hyperlipidemia.

Also, in certain cases where hypolipidemic agents are combined for use, there is the possibility that they are accompanied by a side effect. This is evident, for example, from "N. Engl. J. Med., Vol. 318, No. 1, p 46–47, Jan. 7, 1988," in which D. J. Norman et al. disclose that sarcolysis and acute kidney failure occur in heart transplantation patients receiving the combination of lovastatin and nicotinic acid. The sustainedly released medicinal compositions of this invention rely on the use of the above-mentioned hypolipidemic agents in combination with the sustainedly releasing agents comprising non-crosslinked type anion-exchange resins as described above which possess a cholesterol lowering effect of their own in addition to a sustained release action; and therefore, they are also useful for attenuating such a side effect.

In a sustainedly released medicinal composition of this invention, a non-crosslinked type anion-exchange resin having a sustained release action of a medicine is combined with a medicinally effective amount of the medicine (preferably a hypolipidemic agent as described above) and the composition is preferably used for oral administration.

The weight ratio of a usable hypolipidemic agent to the non-crosslinked type anion-exchange resin is not particularly limited, but they are dispensed where appropriate, preferably within the range of from 0.001:1 to 10:1 and more preferably within the range of from 0.01:1 to 5:1.

The sustainedly released medicinal compositions of this invention exert unexpected and unique effects in the treatment of hyperlipidemia in that they provide an additional anticholesterolemia effect beyond that obtained by the use of their respective active ingredients alone. Thus, even if each dose of the medicine (preferably a hypolipidemic agent) and the non-crosslinked type anion-exchange resin as described above is reduced, their synergism accomplishes the desired pharmacological effects; and further, such a side effect can also be alleviated. Moreover, the non-crosslinked type anion-exchange resins, according to this invention, as described above have a sustained release action of medicines to be combined for use and provide their effects with a lasting action; therefore, the desired pharmacological effects are more efficaciously achieved over a longer period.

Although the reason that the sustainedly releasing agents comprising non-crosslinked type anion-exchange resins of the general formula (I) as described above exert such a sustained release action is not clear, the present inventors interpret it as what follows. The non-crosslinked type anion-exchange resins represented by the general formula (I) as described exhibit water-absorbing ability, which is their physical property; and when they absorb water, they form a gel and dissolve in water finally. Further, they have adequate viscosity in a proper amount of water and can maintain their fluidity in the body. Owing to such physical properties, the object of sustainedly releasing a medicine (preferably a hypolipidemic agent) is therefore achieved unexpectedly. Namely, when the medicine and a non-crosslinked type anion-exchange resin represented by the general formula (I) as described above (the sustainedly releasing agent of this invention) are blended to dispense their preparation and, for example, administered orally; the tablet form of the preparation is disintegrated in the body and the bases for sustained release in the tablets gradually absorb water in the body to form a gel; and it forms the state in which an efficacious ingredient that is the medicine has been incorporated within. Furthermore, as it absorbs the water in the body, the incorporation of the efficacious ingredient is lessened and the medicine is gradually released in a stomach or lower alimentary canal in the body. Accordingly, the sustainedly releasing agents of this invention are believed to be sufficiently effective as bases that aim at sustainedly releasing the efficacious ingredients.

When the sustainedly released medicinal compositions of this invention comprising the sustainedly releasing agents for medicines are to be used for treatment, they may be administered to mammals such as monkey, dog, cat, rat, and human. Such sustainedly released medicinal compositions can be compounded into ordinary dosage forms for oral administration such as tablets, granules, and capsules: tablets and capsules for oral administration are more preferable. Also, when the above-mentioned dosage forms are formulated, carrier substances, excipients, disintegrators, binders, lubricants, buffers, antibacterial agents, fillers, antioxidants, and the like may be included if necessary.

Dosages for a sustainedly released medicinal composition of this invention should carefully be adjusted depending on the age, weight, and condition of the subject, as well as on the route and dosage form of administration, daily regulations, and the desired results. Specifically, for the oral administration to obtain satisfactory results, where the HMG-CoA reductase inhibitor is for example pravastatin, doses within the range of 1–100 mg may be used; and the non-crosslinked type anion-exchange resin to be combined with this reductase inhibitor may be used in doses within the range of 1–2,000 mg, preferably within the range of 1–500 mg. In this case it is preferred that the HMG-CoA reductase inhibitor and the non-crosslinked type anion-exchange resin be used in the same dosage form for oral administration. The sustainedly released medicinal composition of this invention comprising the sustainedly releasing agent for medicines can be administered in one dose or two to four divided doses per day using the above-mentioned dosage forms. For administration to the subject, it is advisable to start in small doses and thereafter gradually increase to large doses.

The sustainedly released medicinal composition of this invention comprising the sustainedly releasing agent for medicines preferably contains one or plural kinds of active ingredients in doses within the above-mentioned ranges, the reminder being physiologically acceptable carriers or other substances acceptable in standard medical practice; for example, tablets in various dimensions in a total amount of 2–2,000 mg can be manufactured. The sustainedly released medicinal composition of this invention can be made into gelatin capsules in like manner and such dosage forms can be administered to the subject one to four times daily.

When the sustainedly released medicinal compositions of this invention comprising the sustainedly releasing agents for medicines are to be compounded, it is possible to combine the above-mentioned active ingredients in their individual types of unit dosage forms for administration with physiologically acceptable carriers, excipients, binders, preservatives, stabilizers, flavoring agents, and the like, according to standard medical practice. Among the concrete examples of adjuvants that can be added to tablets, mentioned are binders such as traganth gum, arabic gum, crystalline cellulose, corn starch, and gelatin; excipients such as anhydrous calcium hydrogenphosphate, lactose, and cellulose; lubricants such as corn starch, potato starch, and magnesium alginate; sweetening agents such as sucrose, aspartame, and saccharin; and flavoring agents such as orange, peppermint, wintergreen oil and cherry. Further, when unit dosage forms for administration are capsules, the capsules may contain liquid carriers such as fatty oil in addition to the above-mentioned kinds of substances. Furthermore, a variety of other substances may be present together to alter the physical states of the unit dosage forms for administration, or as a coating. For example, tablets or capsules may be coated with either or both of shellac and sugar.

Further, some of the above-mentioned active ingredients form medicinally acceptable salts generally known such as alkaline metal salts and other ordinary basic or acid addition salts. Thus, reference to fundamental substances in the present specification is intended to encompass ordinary salts of their compounds that can be regarded as being substantially equivalent to the compounds as described.

The sustainedly released medicinal compositions of this invention may be administered over a long period, namely four weeks to six months or longer, as long as serum cholesterol levels are high, for example. They can also be used as sustainedly released medicinal compositions capable of providing prescribed doses at intervals of once or twice a week, or once a month, and administration periods of at least one to two weeks are preferable for the purpose of obtaining minimum efficacy.

This invention will be more concretely explained on the basis of preferred Examples of the invention as well as Comparative Examples; however, the invention should not be limited to these examples.

Preparation of Non-crosslinked Type Anion-exchange Resins

Acryloyloxyethyl-N,N-dimethylamine (85.9 g, 0.6 mol), acetone (160 g), and hydroquinone monomethyl ether (0.1 g) as a polymerization inhibitor were added to a double neck flask equipped with a reflux condenser and dropping funnel and mixed uniformly. Benzyl chloride (75.9 g, 0.6 mol) was added dropwise to the mixed solution obtained over about 15 min and it was allowed to stand overnight with stirring at room temperature. The resulting reaction product was washed with 500 ml of acetone to afford crystals of 14 E-acryloyloxyethyl-N,N-dimethylbenzylammonium chloride.

The crystals of acryloyloxyethyl-N,N-dimethylbenzylammonium chloride obtained (150 g) were dissolved in 280 g of purified water in a three neck separable flask equipped with a reflux condenser and the atmosphere in the flask was substituted with nitrogen for 5 h. The resulting solution was maintained at a reaction temperature of 65° C. and to this was added 0.01 g of 2,2'-azobis(2-amidinopropane) hydrochloride as a polymerization initiator. After reaction for about 20 h, the resulting reaction product was precipitated in acetone to afford the non-crosslinked type anion-exchange resin, according to this invention, represented by the following structural formula (III):

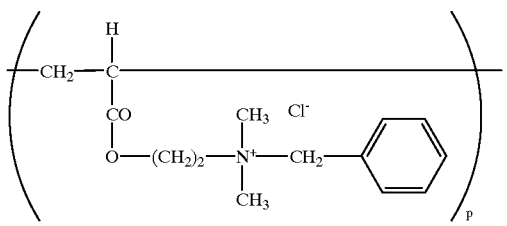

The non-crosslinked type anion-exchange resin thus obtained was used in the following Examples and Comparative Examples.

| COMPARATIVE EXAMPLE 1 | |
|---|---|
| ingredients | weight part |
| pravastatin | 10 |
| lactose | 64 |
| microcrystalline cellulose | 20 |
| crosscarmellose sodium | 2 |
| magnesium stearate | 1 |
| magnesium oxide | 3 |

A pravastatin preparation in tablet forms containing the above-mentioned various ingredients was produced according to the procedure that follows. Specifically, the pravastatin, magnesium oxide, and a portion of lactose (30%) as described above were blended with a suitable mixer for 2–10 min. The resulting mixture was passed through a #12–40 mesh size screen. Microcrystalline cellulose, crosscarmellose sodium and the remaining lactose were added to the mixture and the resulting mixture was blended for 2–10 min. Subsequently, magnesium stearate was added to the mixture and blending continued for 1–3 min. Further, the resulting homogeneous mixture was subjected to tablet making to afford tablets containing 10 mg of pravastatin for the prevention or treatment of hyperlipidemia.

| COMPARATIVE EXAMPLE 2 | |
|---|---|
| ingredients | weight part |
| pravastatin | 27 |
| lactose | 47 |
| microcrystalline cellulose | 20 |
| crosscarmellose sodium | 2 |
| magnesium stearate | 1 |
| magnesium oxide | 3 |

A pravastatin preparation in tablet forms containing the above-mentioned various ingredients was produced according to the procedure that follows. Specifically, the pravastatin, magnesium oxide, and a portion of lactose (30%) as described above were blended with a suitable mixer for 2–10 min. The resulting mixture was passed through a #12–40 mesh size screen. Microcrystalline cellulose, crosscarmellose sodium and the remaining lactose were added to the mixture and the resulting mixture was blended for 2–10 min. Subsequently, magnesium stearate was added to the mixture and blending continued for 1–3 min. Further, the resulting homogeneous mixture was subjected to tablet making to afford tablets containing 54 mg of pravastatin for the prevention or treatment of hyperlipidemia.

COMPARATIVE EXAMPLE 3

| ingredients | weight part |
|---|---|
| the non-crosslinked type anion-exchange resin | 89 |
| microcrystalline cellulose | 10 |
| light silicic acid anhydride | 0.5 |
| magnesium stearate | 0.5 |

A non-crosslinked type anion-exchange resin preparation in tablet forms containing the above-mentioned various ingredients was produced according to the procedure that follows. Specifically, microcrystalline cellulose and light silicic acid anhydride were blended with a suitable mixer for 2–10 min. Next, the total amount of the non-crosslinked type anion-exchange resin was divided into four portions and each portion was added to the aforementioned mixture at 5-min intervals and blended. Subsequently, magnesium stearate was taken and weighed, added to the mixer and blended for 1 min. Further, the resulting homogeneous mixture was subjected to tablet making to afford tablets containing 200 mg of the non-crosslinked type anion-exchange resin for the prevention or treatment of hyperlipidemia.

COMPARATIVE EXAMPLE 4

| ingredients | weight part |
|---|---|
| the non-crosslinked type anion-exchange resin | 75 |
| microcrystalline cellulose | 24 |
| light silicic acid anhydride | 0.5 |
| magnesium stearate | 0.5 |

A non-crosslinked type anion-exchange resin preparation in tablet forms containing the above-mentioned various ingredients was produced according to the procedure that follows. Specifically, microcrystalline cellulose and light silicic acid anhydride were blended with a suitable mixer for 2–10 min. Next, the total amount of the non-crosslinked type anion-exchange resin was divided into four portions and each portion was added to the aforementioned mixture at 5-min intervals and blended. Subsequently, magnesium stearate was taken and weighed, added to the mixer and blended for 1 min. Further, the resulting homogeneous mixture was subjected to tablet making to afford tablets containing 150 mg of the non-crosslinked type anion-exchange resin for the prevention or treatment of hyperlipidemia.

EXAMPLE 1

| ingredients | weight part |
|---|---|
| the non-crosslinked type anion-exchange resin | 89 |
| pravastatin | 0.89 |
| microcrystalline cellulose | 9.11 |
| light silicic acid anhydride | 0.5 |
| magnesium stearate | 0.5 |

Tablets (preparation in tablet forms) containing pravastatin and the non-crosslinked type anion-exchange resin, which contain the above-mentioned various ingredients, were produced according to the procedure that follows. Specifically, the pravastatin, microcrystalline cellulose and light silicic acid anhydride as described above were blended with a suitable mixer for 2–10 min. Next, the total amount of the non-crosslinked type anion-exchange resin was divided into four portions and each portion was added to the aforementioned mixture at 5-min intervals and blended. Subsequently, magnesium stearate was taken and weighed, added to the mixer and blended for 1 min. Further, the resulting homogeneous mixture was subjected to tablet making to afford tablets containing 2 mg of pravastatin and 200 mg of the non-crosslinked type anion-exchange resin for the prevention or treatment of hyperlipidemia.

EXAMPLE 2

| ingredients | weight part |
|---|---|
| the non-crosslinked type anion-exchange resin | 75 |
| pravastatin | 6.75 |
| microcrystalline cellulose | 17.25 |
| light silicic acid anhydride | 0.5 |
| magnesium stearate | 0.5 |

Tablets (preparation in tablet forms) containing pravastatin and the non-crosslinked type anion-exchange resin, which contain the above-mentioned various ingredients, were produced according to the procedure that follows. Specifically, the pravastatin, microcrystalline cellulose and light silicic acid anhydride as described above were blended with a suitable mixer for 2–10 min. Next, the total amount of the non-crosslinked type anion-exchange resin was divided into four portions and each portion was added to the aforementioned mixture at 5-min intervals and blended. Subsequently, magnesium stearate was taken and weighed, added to the mixer and blended for 1 min. Further, the resulting homogeneous mixture was subjected to tablet making to afford tablets containing 13.5 mg of pravastatin and 150 mg of the non-crosslinked type anion-exchange resin for the prevention or treatment of hyperlipidemia.

EXAMPLE 3

| ingredients | weight part |
|---|---|
| the non-crosslinked type anion-exchange resin | 64 |
| clofibrate | 24 |
| microcrystalline cellulose | 11 |
| light silicic acid anhydride | 0.5 |
| magnesium stearate | 0.5 |

Tablets (preparation in tablet forms) containing clofibrate and the non-crosslinked type anion-exchange resin, which contain the above-mentioned various ingredients, were produced according to the procedure that follows. Specifically, the clofibrate, microcrystalline cellulose and light silicic acid anhydride as described above were blended with a suitable mixer for 2–10 min. Next, the total amount of the non-crosslinked type anion-exchange resin was divided into four portions and each portion was added to the aforementioned mixture at 5-min intervals and blended. Subsequently, magnesium stearate was taken and weighed, added to the mixer and blended for 1 min. Further, the resulting homogeneous mixture was subjected to tablet making to afford tablets containing 75 mg of clofibrate and 200 mg of the non-crosslinked type anion-exchange resin for the prevention or treatment of hyperlipidemia.

EXAMPLE 4

| ingredients | weight part |
| --- | --- |
| the non-crosslinked type anion-exchange resin | 70 |
| nicomol | 21 |
| microcrystalline cellulose | 8 |
| light silicic acid anhydride | 0.5 |
| magnesium stearate | 0.5 |

Tablets (preparation in tablet forms) containing nicomol and the non-crosslinked type anion-exchange resin, which contain the above-mentioned various ingredients, were produced according to the procedure that follows. Specifically, the nicomol, microcrystalline cellulose and light silicic acid anhydride as described above were blended with a suitable mixer for 2–10 min. Next, the total amount of the non-crosslinked type anion-exchange resin was divided into four portions and each portion was added to the aforementioned mixture at 5-min intervals and blended. Subsequently, magnesium stearate was taken and weighed, added to the mixer and blended for 1 min. Further, the resulting homogeneous mixture was subjected to tablet making to afford tablets containing 60 mg of nicomol and 200 mg of the non-crosslinked type anion-exchange resin for the prevention or treatment of hyperlipidemia.

TESTING EXAMPLE 1
(In Vitro Elution Test of Pravastatin Tablets and Tablets Containing Pravastatin and the Non-crosslinked Type Anion-exchange Resin)

The pravastatin tablets prepared in Comparative Example 1 and the tablets containing pravastatin and the non-crosslinked type anion-exchange resin prepared in Example 1 were used to conduct the elution test of pravastatin according to "1 Elution Test Methods (Paddle method)" in the Pharmacopoeia of Japan. In addition, the agitation speed in the test was set to 50 rpm. The results obtained are shown in Table 1 as described below.

TABLE 1

| elution solution | time to reach the elution percentage (*1) | pravastatin (Comparative Example 1) | tablet containing pravastatin and the non-crosslinked type anion-exchange resin (Example 1) |
| --- | --- | --- | --- |
| pH1.2 solution (1st solution: The Pharmacopoeia) | T75% | 6.1 (min) | 197.0 (min) |
| | T95% | 7.9 (min) | 237.1 (min) |
| pH4.0 solution 0.1M (1st solution: The Pharmacopoeia) | T75% | 4.3 (min) | 165.35 (min) |
| | T95% | 5.6 (min) | 209.2 (min) |
| pH6.8 solution (2nd solution: The Pharmacopoeia) | T75% | 7.0 (min) | 165.1 (min) |
| | T95% | 9.8 (min) | 210.4 (min) |

(*1) Times for the elution percentage of pravastatin to reach 75% and 95% were determined, respectively; and the time to reach 75% was designated "T75%" and the time to reach 95%, "T95%".

From the results shown in Table 1, it was apparent that where the tablets containing pravastatin and the non-crosslinked type anion-exchange resin were used (Example 1), the elution of pravastatin was slow as compared to the case where the pravastatin tablets were used alone (Comparative Example 1). In other words, it was ascertained that the non-crosslinked type anion-exchange resins according to this invention sustainedly release pravastatin and the efficacy of pravastatin is more sustainedly manifested.

TESTING EXAMPLE 2
(Test 1 on the Control of the Rise of Blood Cholesterol in NZW Male Rabbits Fed Cholesterol Load)

Employing NZW rabbits fed cholesterol load, experiments on the controlling effect on the rise of blood cholesterol were performed as described below in the following cases: where the 10 mg pravastatin tablets prepared in Comparative Example 1 (1 tablet per day) were used; where the 200 mg non-crosslinked type anion-exchange resin tablets prepared in Comparative Example 3 (5 tablets per day) were used; where the tablets containing 2 mg of pravastatin and 200 mg of the non-crosslinked type anion-exchange resin prepared in Example 1 (5 tablets per day) were used; and where the 10 mg pravastatin tablets prepared in Comparative Example 1 (1 tablet per day) and the 200 mg non-cross linked type anion-exchange resin tablets prepared in Comparative Example 3 (5 tablets per day) were used together.

Specifically, the NZW male rabbits were fed chow containing 0.67% cholesterol for 21 days. On the 7th day after the start of cholesterol loading, the NZW male rabbits were divided into groups so that the total serum cholesterol level in each group was almost equal. From the 8th day after the start of cholesterol loading, oral administration of each of the above-mentioned medicinal compositions continued for 14 days. On the day when the medicine administration started and the 14th day thereafter, blood was collected to measure the total serum cholesterol levels for comparison. The results obtained are shown in FIG. 1.

From the results shown in FIG. 1, it was apparent that where the tablets containing 2 mg of pravastatin and 200 mg of the non-crosslinked type anion-exchange resin (5 tablets per day) were used (Example 1), there were no significant differences in the controlling effect of the rise of blood cholesterol when compared to the case where only the 200 mg non-crosslinked type anion-exchange resin tablets (5 tablets per day) were used (Comparative Example 3), or the case where the 10 mg pravastatin tablets (1 tablet per day) and the 200 mg non-crosslinked type anion-exchange resin tablets (5 tablets per day) were used together (Comparative Example 1 plus Comparative Example 3). On the other hand, where the tablets containing 2 mg of pravastatin and 200 mg of the non-crosslinked type anion-exchange resin (5 tablets per day) were used (Example 1), the controlling effect of the rise of blood cholesterol was greater than the case where only the 10 mg pravastatin tablets (1 tablet per day) were used (Comparative Example 1). Accordingly, it was ascertained that the tablets according to this invention containing pravastatin and the non-crosslinked type anion-exchange resin are able to markedly control the rise of blood cholesterol as compared to the pravastatin tablets only, and are very effective in the treatment of hyperlipidemia.

TESTING EXAMPLE 3
(Test 2 on Control of the Rise of Blood Cholesterol in NZW Male Rabbits Fed Cholesterol Load)

Employing NZW rabbits fed cholesterol load, experiments on the controlling effect on the rise of blood cholesterol were performed as described below in the following cases: where the 54 mg pravastatin tablets prepared in Comparative Example 2 (1 tablet per day) were used; where the 150 mg non-crosslinked type anion-exchange resin tablets prepared in Comparative Example 4 (4 tablets per day) were used; where the tablets containing 13.5 mg of pravastatin and 150 mg of the non-crosslinked type anion-exchange resin prepared in Example 2 (4 tablets per day) were used; and where the 54 mg pravastatin tablets prepared in Comparative Example 2 (1 tablet per day) and the 150 mg non-cross linked type anion-exchange resin tablets prepared in Comparative Example 4 (4 tablets per day) were used together.

Specifically, the NZW male rabbits were fed chow containing 0.67% cholesterol for 21 days. On the 7th day after the start of cholesterol loading, the NZW male rabbits were divided into groups so that the total serum cholesterol level in each group was almost equal. From the 8th day after the start of cholesterol loading, oral administration of each of the above-mentioned medicinal compositions continued for 14 days. On the day when the medicine administration started and the 14th day thereafter, blood was collected to measure the total serum cholesterol levels for comparison. The results obtained are shown in FIG. 2.

From the results shown in FIG. 2, it was apparent that where the tablets containing 13.5 mg of pravastatin and 150 mg of the non-crosslinked type anion-exchange resin (4 tablets per day) were used (Example 2), there exhibited a significant controlling effect of the rise of blood cholesterol when compared to the case where only the 54 mg pravastatin tablets (1 tablets per day) were used (Comparative Example 2) and the case where only the 150 mg non-crosslinked type anion-exchange resin tablets (4 tablets per day) were used (Comparative Example 4). Furthermore, where the tablets containing 13.5 mg of pravastatin and 150 mg of the non-crosslinked type anion-exchange resin (4 tablets per day) were used (Example 2), the controlling effect of the rise of blood cholesterol was greater even than the case where the 54 mg pravastatin tablets (1 tablet per day) and the 150 mg non-crosslinked type anion-exchange resin tablets (4 tablets per day) were used together (Comparative Example 2 plus Comparative Example 4). Accordingly, it was ascertained that the tablets according to this invention containing pravastatin and the non-crosslinked type anion-exchange resin are able to markedly control the rise of blood cholesterol as compared with the use of pravastatin tablets alone, the use of non-crosslinked type anion-exchange resin tablets alone, or the combined use of pravastatin tablets and non-crosslinked type anion-exchange resin tablets, and are very effective in the treatment of hyperlipidemia.

TEST EXAMPLE 4
(Measurement of the Variation of Blood Concentrations of Pravastatin in NZW Male Rabbits)

A 54 mg pravastatin tablet (I tablet) prepared in Comparative Example 2 and tablets (4 tablets) prepared in Example 2 containing 13.5 mg of pravastatin and 150 mg of the non-crosslinked type anion-exchange resin were orally administered to NZW male rabbits at a single time, respectively. Plasma concentrations of pravastatin were measured to find AUC (ng/ml·h) and $T_{max}$ (h).

As a result, AUC showed almost no variation and $T_{max}$ increased in the case where the tablet containing pravastatin and the non-crosslinked type anion-exchange resin was used, as compared with the case where the pravastatin tablet alone was used. Accordingly, it was ascertained that in a tablet containing pravastatin and the non-crosslinked type anion-exchange resin, the non-crosslinked type anion-exchange resin sustainedly releases pravastatin and the efficacy of pravastatin is more sustainedly manifested.

INDUSTRIAL APPLICABILITY

The non-crosslinked type anion-exchange resins according to this invention possess hydrophobic groups while being non-crosslinked anion-exchange resins; therefore, the sustainedly releasing agents of the invention comprising the non-crosslinked type anion-exchange resins as described above have enabled the sustained release of such medicines over a longer period with more steadiness even where anionic or liposoluble medicines are particularly chosen as active ingredients.

Further, the non-crosslinked type anion-exchange resins according to this invention possess a controlling effect on the rise of cholesterol of their own in addition to the sustained release effect as described above; therefore, the sustainedly released medicinal compositions of the invention in which the sustainedly releasing agents comprising the non-crosslinked anion-exchange resins and hypolipidemic agents are combined for use have produced synergism of the blood cholesterol lowering effects by both ingredients as described above, and at the same time have enabled the sustained action of the hypolipidemic agents over a long period with more steadiness.

What is claimed is:

1. A sustainedly released medicinal composition comprising a sustainedly releasing agent for medicines and a medicine having a hypolipidemic effect, said sustainedly releasing agent comprising a non-crosslinked type anion-exchange resin represented by the following general formula (I):

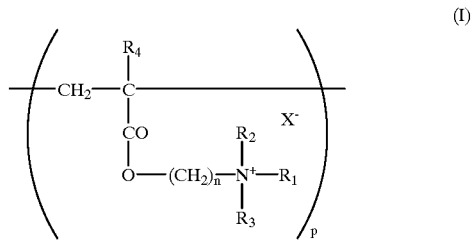

wherein
R$^1$ represents a moiety selected from the group consisting of aralkyl groups of 7–10 carbons and alkyl groups of 1–20 carbons;
R$^2$ and R$^3$ may be the same or different and each represents a hydrogen atom or a lower alkyl group;
x$^-$ represents a physiologically acceptable counter ion;
n represents 1–3; and
p represents a mean degree of polymerization, respectively; and
said medicine having a hypolipidemic effect is at least one medicine selected from the group consisting of probucol, a clofibrate-containing medicine, a nicotininc acid-containing medicine, a squalene synthetase inhibitor, a squalene epoxidase inhibitor, a hydroxymethylglutaryl coenzyme A reductase inhibitor, and an acyl coenzyme A: cholesterol acyl transferase inhibitor.

2. The sustainedly released medicinal composition according to claim 1, wherein R$_1$ is benzyl, R$_2$ is methyl, R$_3$ is methyl, R$_4$ is a hydrogen atom, X$^-$ is a chlorine ion, and n is 2.

3. The sustainedly released medicinal composition according to claim 1, wherein the weight ratio of the medicine having a hypolipidemic effect to the non-crosslinked anion-exchange resin is within the range of from 0.001:1 to 10:1.

4. The sustainedly released medicinal composition according to claim 1, wherein the medicine having a hypolipidemic effect is dispersed in the non-crosslinked anion-exchange resin.

5. The sustainedly released medicinal composition according to claim 1, wherein p represents a mean degree of polymerization of 20 to 20,000.

* * * * *